US011365165B2

(12) United States Patent
Pan et al.

(10) Patent No.: US 11,365,165 B2
(45) Date of Patent: Jun. 21, 2022

(54) ORGANIC BASE MODIFIED COMPOSITE CATALYST AND METHOD FOR PRODUCING ETHYLENE BY HYDROGENATION OF CARBON MONOXIDE

(71) Applicant: DALIAN INSTITUTE OF CHEMICAL PHYSICS, CHINESE ACADEMY OF SCIENCES, Dalian (CN)

(72) Inventors: Xiulian Pan, Dalian (CN); Feng Jiao, Dalian (CN); Xinhe Bao, Dalian (CN)

(73) Assignee: DALIAN INSTITUTE OF CHEMICAL PHYSICS, CHINESE Academy of Sciences, Dalian (CN)

( * ) Notice: Subject to any disclaimer, the term of this patent is extended or adjusted under 35 U.S.C. 154(b) by 133 days.

(21) Appl. No.: 16/963,070

(22) PCT Filed: Jan. 28, 2019

(86) PCT No.: PCT/CN2019/073387
§ 371 (c)(1),
(2) Date: Jul. 17, 2020

(87) PCT Pub. No.: WO2019/144953
PCT Pub. Date: Aug. 1, 2019

(65) Prior Publication Data
US 2020/0346992 A1 Nov. 5, 2020

(30) Foreign Application Priority Data
Jan. 26, 2018 (CN) .......................... 201810079670.5

(51) Int. Cl.
*B01J 29/06* (2006.01)
*C07C 1/04* (2006.01)
*B01J 29/24* (2006.01)
*B01J 29/26* (2006.01)
*B01J 35/10* (2006.01)
*B01J 23/26* (2006.01)
*B01J 23/16* (2006.01)
*B01J 23/75* (2006.01)
*B01J 23/22* (2006.01)
*B01J 23/34* (2006.01)
*B01J 23/745* (2006.01)
*B01J 29/18* (2006.01)
*B01J 29/22* (2006.01)
*B01J 37/08* (2006.01)
(Continued)

(52) U.S. Cl.
CPC ................ *C07C 1/04* (2013.01); *B01J 23/16* (2013.01); *B01J 23/22* (2013.01); *B01J 23/26* (2013.01); *B01J 23/34* (2013.01); *B01J 23/745* (2013.01); *B01J 23/75* (2013.01); *B01J 29/18* (2013.01); *B01J 29/185* (2013.01); *B01J 29/22* (2013.01); *B01J 29/24* (2013.01); *B01J 29/26* (2013.01); *B01J 35/1014* (2013.01); *B01J 35/1019* (2013.01); *B01J 37/08* (2013.01); *C07C 1/043* (2013.01); *C07C 1/0435* (2013.01); *C07C 1/0445* (2013.01); *B01J 2229/14* (2013.01); *B01J 2229/186* (2013.01); *B01J 2229/20* (2013.01); *B01J 2229/34* (2013.01); *C07C 11/04* (2013.01); *C07C 11/06* (2013.01); *C07C 2523/10* (2013.01); *C07C 2523/745* (2013.01); *C07C 2523/75* (2013.01); *C07C 2529/24* (2013.01); *Y02P 20/52* (2015.11)

(58) Field of Classification Search
CPC .. Y02P 20/52; B01J 23/06; B01J 23/08; B01J 23/16; B01J 23/26; B01J 23/745; B01J 23/75; B01J 23/34; B01J 29/22; B01J 29/24; B01J 29/26; B01J 29/18; B01J 29/185; B01J 2229/14; B01J 2229/34; B01J 2229/186; B01J 2229/20; B01J 35/1014; B01J 35/1019; B01J 37/08; C07C 1/043; C07C 1/0445; C07C 1/0435; C07C 1/04; C07C 2523/08; C07C 2523/06; C07C 2523/26; C07C 2523/18; C07C 2523/10; C07C 2523/34; C07C 2523/75; C07C 2523/745; C07C 11/04; C07C 11/06; C07C 2529/18; C07C 2529/24
USPC ........ 502/60, 61, 62, 64, 66, 69, 74, 78, 85, 502/155, 162, 167; 585/638
See application file for complete search history.

(56) References Cited

U.S. PATENT DOCUMENTS

2010/0105548 A1  4/2010  Zhang et al.
2010/0263534 A1*  10/2010  Chuang ................ B01J 20/3257
                                                95/139
(Continued)

FOREIGN PATENT DOCUMENTS

CN    101722304 A    6/2010
CN    105688872 A    6/2016
(Continued)

OTHER PUBLICATIONS

Machine Translation of CN 101722034, claims, pp. 1-2, 2010.*
(Continued)

*Primary Examiner* — Elizabeth D Wood
(74) *Attorney, Agent, or Firm* — MagStone Law, LLP; Enshan Hong

(57) ABSTRACT

An organic base modified composite catalyst for producing ethylene by hydrogenation of carbon monoxide is a composite catalyst and formed by compounding component I and component II in a mechanical mixing mode. The active ingredient of the component I is a metal oxide; the component II is an organic base modified zeolite of MOR topology; and a weight ratio of the active ingredients in the component I to the component II is 0.1-20, and preferably 0.3-8. The reaction process has an extremely high product yield and selectivity. The selectivity of $C_2$-$C_3$ olefins is as high as 78-87%; the selectivity of hydrocarbon products with more than 4 C atoms is less than 10%; the selectivity of a methane side product is extremely low (<9%); and meanwhile, the selectivity of the ethylene is 75-82%.

12 Claims, No Drawings

(51) Int. Cl.
*C07C 11/04* (2006.01)
*C07C 11/06* (2006.01)

(56) References Cited

U.S. PATENT DOCUMENTS

| | | | |
|---|---|---|---|
| 2012/0263534 A1* | 10/2012 | Heller | G05B 19/106 |
| | | | 405/3 |
| 2014/0256537 A1* | 9/2014 | Chinta | B01J 29/86 |
| | | | 502/167 |
| 2018/0194700 A1 | 7/2018 | Pan et al. | |
| 2019/0344252 A1* | 11/2019 | Cho | B01J 29/85 |

FOREIGN PATENT DOCUMENTS

| | | |
|---|---|---|
| CN | 106311317 A | 1/2017 |
| CN | 106345514 A | 1/2017 |
| CN | 108927132 A | 12/2018 |

OTHER PUBLICATIONS

Machine Translation of CN 101722034, description, pp. 1-8, 2010.*
Written Opinion dated Apr. 26, 2019 for related International Patent Application No. PCT/CN2019/073387 issued by the international searching authority.
International Search Report dated Apr. 26, 2019 for related International Patent Application No. PCT/CN2019/073387 issued by the international searching authority.

* cited by examiner

ORGANIC BASE MODIFIED COMPOSITE CATALYST AND METHOD FOR PRODUCING ETHYLENE BY HYDROGENATION OF CARBON MONOXIDE

RELATED APPLICATIONS

This is a U.S. national stage of international application No. PCT/CN2019/073387 filed on Jan. 28, 2019, which claims priority from China Patent Application No. 201810079670.5 filed on Jan. 26, 2018, the entire content of which is incorporated herein as reference.

TECHNICAL FIELD

The present invention belongs to preparation of high-value chemicals such as light olefin by hydrogenation of carbon monoxide, and particularly relates to an organic base modified composite catalyst and a method for producing ethylene by hydrogenation of carbon monoxide.

BACKGROUND

Ethylene is very important basic chemical raw material and one of the chemical products with the maximum production in the world. The ethylene industry is the core of the petrochemical industry and occupies an important position in the national economy. Light olefin refers to alkene with the number of carbon atoms less than or equal to 4. Light olefin represented by ethylene and propylene are very important basic organic chemical raw materials. With the fast growth of economy in China, the ethylene industry of China has developed rapidly, and occupies an important position in the world ethylene market. The light olefin market has been in short supply for a long time. At present, ethylene is produced mainly by a petrochemical route of naphtha and light diesel cracking or a technology of ethane cracking. Because the petroleum of China has relied on imports for long time, the energy security of China has great risks, and it is urgent to develop an ethylene production technology independent of the petroleum. Coal, natural gas, biomass and other renewable materials are converted into a mixture of carbon monoxide and hydrogen, i.e., syngas. The ratio of the carbon monoxide to the hydrogen in the syngas is changed with different raw materials. The syngas is used as raw material. After the ratio of the carbon monoxide to the hydrogen is adjusted to an appropriate value, the carbon monoxide and the hydrogen generate a Fischer-Tropsch synthesis reaction under the action of a proper catalyst to produce light olefin with the number of carbon atoms less than or equal to 4. In this way, the olefin can be produced in one step. The route provides an alternative solution for the production of the ethylene by a naphtha cracking technology. The technology simplifies the process flow and greatly reduces the investment unlike an indirect method that further prepares the alkene from the syngas and the methanol or dimethyl ether.

Direct preparation of the light olefin through Fischer-Tropsch synthesis has become one of research hotspots in direct production of the olefin using the syngas. In patent CN1083415A disclosed by Dalian Institute of Chemical Physics, Chinese Academy of Sciences, high activity (CO conversion rate: 90%) and selectivity (light olefin selectivity: 66%) can be obtained under reaction pressure of 1.0 to 5.0 MPa and reaction temperature of 300 to 400° C. in preparation of the light olefin from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University Of Chemical Technology, Fe/activated carbon catalyst with manganese, copper, zinc, silicon and potassium as auxiliaries is prepared by a vacuum impregnation method for the reaction of preparation of the light olefin from the syngas. Under the condition of no feedstock gas circulation, the CO conversion rate is 96%, and the selectivity of the light olefin in hydrocarbons is 68%. In the above report, the catalyst uses metal iron or iron carbide as the active ingredient. The reaction follows the chain growth reaction mechanism of metal surfaces. The selectivity of the product light olefin is low, and especially, the selectivity of a single product such as ethylene is less than 30%. In 2016, researcher Sun Yuhan and researcher Zhong Liangshu in Shanghai Advanced Research Institute reported a preferred exposure [101] and [020] manganese-assisted cobalt carbide based catalyst, and realized 60.8% of selectivity of light olefin and 5% of selectivity of methane at a CO conversion rate of 31.8%. However, the selectivity of single ethylene is less than 20%. A composite bifunctional catalyst of $ZnCr_2O_4$ oxide and hierarchical pore SAPO-34 zeolite has been reported by academician Bao Xinhe and researcher Pan Xiulian in Dalian Institute of Chemical Physics, Chinese Academy of Sciences (Jiao et al., Science 351 (2016) 1065-1068), which has realized 80% of selectivity of the light olefin when the conversion rate of CO is 17%. However, the selectivity of the ethylene is less than 30%. In the applied patent 201710129620.9, a bifunctional catalyst containing a combination of oxygen vacancies and MOR zeolite is used in a one-step reaction of producing olefin from syngas, so that the selectivity of the ethylene is increased to 75-80%. However, more hydrocarbons with more than 3 carbon atoms in the side product affect the application of the technology. The present invention further reduces the selectivity of a methane side product to be less than 9% by adjusting the acidic characteristics of the MOR zeolite, and the selectivity of hydrocarbons above $C_4$ is also further reduced.

SUMMARY OF THE INVENTION

The technical problem of the present invention: the present invention overcomes the defects of the prior art and provides a base modified catalyst and a method for producing ethylene by hydrogenation of carbon monoxide. The invented catalyst can catalyze the reaction of carbon monoxide and hydrogen to directly produce light olefin; the selectivity of $C_2$-$C_3$ olefins is as high as 78-87%; the selectivity of a single product of ethylene can be as high as 75-82%; the selectivity of methane is less than 9%; and hydrocarbon selectivity of $C_4$ and above is less than 10%.

The technical solution of the present invention is: a catalyst comprises component I and component II; the component I and the component II are compounded in a mechanical mixing mode; an active ingredient of the component I is a metal oxide; the component II is a zeolite of MOR topology; in the component II, the zeolite of the MOR topology is modified with fatty amine; and the modification treatment is to disperse the fatty amine into B acid sites in 12-ring porous channels of the zeolite of the MOR topology.

The fatty amine is one or more than one of dimethylamine, trimethylamine, diethylamine, triethylamine, ethylenediamine, monopropylamine, dipropylamine, tripropylamine, isopropylamine, diisopropylamine, 1,2-dimethylpropylamine, 1,2-propanediamine, 2-propeneamine, cyclopropylamine, n-butylamine, di-n-butylamine, isobutylamine, sec-butylamine, 1,4-butanediamine, tert-butylamine, diisobutylaminehexylamine, 2-ethylhexylamine, hexamethylenediamine and trioctylamine.

The mechanical mixing in the present invention can adopt one or more than two of mechanical agitation, ball milling, rocking bed mixing and mechanical grinding for composition.

The zeolite of the MOR topology is modified with fatty amine, so as to prevent organic base molecules from entering 8-ring porous channels and enable the organic base molecules to selectively occupy the B acid site of the 12-ring porous channels.

The MOR topology of the present invention is an orthorhombic crystal system, is of a one-dimensional porous channel structure with parallel elliptical straight-through porous channels, and includes 8-ring porous channels and 12-ring one-dimensional porous channels.

The modification of the fatty amine in the present invention means that the B acid sites in the 12-ring porous channels of the MOR zeolite are occupied by using fatty amine molecules, which can be occupied completely or partially. The B acid sites in the 12-ring porous channels are occupied by 50-100%.

All known methods for dispersing the fatty amine to the B acid sites in the 12-ring porous channels of the MOR zeolite capable of achieving the purpose can satisfy requirements. Herein, a vacuum dehydration adsorption method is taken as an example. Firstly, the temperature on a vacuum line is controlled as treatment temperature 350-500° C. of dehydration and degassing on a zeolite sample; the pressure is 1 Pa-10−5 Pa; and the time is 4 h-24 h. Further, the degassed zeolite is exposed to the atmosphere of fatty amine of 10 Pa-100 kPa or the atmosphere of organic base diluted with inert gas; the adsorption temperature is controlled at room temperature −300° C.; and after purging with inorganic gas at 200-330° C. for 30 min-12 h, a fatty amine modified zeolite is obtained.

The metal oxide is one or more than one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$.

The specific surface area of $MnO_x$, $ZnO_x$, $CeO_x$, $GaO_x$, $BiO_x$ and $InO_x$ is 1-100 m²/g; and a preferred specific surface area is 50-100 m²/g.

The specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn(1-a-b)O_x$ and $In_aGa_bMn(1-a-b)O_x$ is 5-150 m²/g; and a preferred specific surface area is 50-150 m²/g.

The value range of x is 0.7-3.7, and the value range of a is 0-1; and the value range of a+b is 0-1.

a, b, (1−a), (1−a−b) and x in the present invention only represent the relative proportions of the chemical composition of the elements in the metal oxide. Any metal oxide with the same proportion is regarded as the same metal oxide.

A weight ratio of the active ingredients in the component I to the component II is 0.1-20, and preferably 0.3-8. Multi-component synergy can ensure that the reaction is conducted effectively, and too much or too little of a component is not conducive to the reaction.

A dispersing agent is also added to the component I; the dispersing agent is one or more than one of $Al_2O_3$, $SiO_2$, $Cr_2O_3$, $ZrO_2$, $TiO_2$, $Ga_2O_3$, activated carbon, graphene and carbon nanotube; the metal oxide is dispersed in the dispersing agent; and the content of the dispersing agent in the component I is 0.05-90 wt %, and preferably 0.05-25 wt %; and the balance is an active metal oxide.

The skeleton element composition of the zeolite of the MOR topology may be one or more than one of Si—Al—O, Ga—Si—O, Ga—Si—Al—O, Ti—Si—O, Ti—Al—Si—O, Ca—Al—O and Ca—Si—Al—O.

A method for preparing ethylene through direct conversion of syngas uses syngas as reaction raw material; the syngas can also include a given amount of carbon dioxide; and a conversion reaction is conducted on a fixed bed or a moving bed. The ethylene can be produced with high selectivity. An adopted catalyst is the above catalyst.

The pressure of the syngas is 0.5-10 MPa, preferably 1-8 MPa and more preferably 2-8 MPa; reaction temperature is 300-600° C., and preferably 300° C.-450° C.; space velocity is 300-10000 $h^{-1}$, preferably 500-9000 $h^{-1}$ and more preferably 500-6000 $h^{-1}$; and higher space time yield can be obtained.

The molar ratio of syngas $H_2/CO$ for the reaction is 0.2-3.5, and preferably 0.3-2.5. The syngas with higher space time yield and selectivity can also include $CO_2$, wherein the volume concentration of $CO_2$ in the syngas is 0.1-50%.

The above catalyst in the present invention is used for preparing ethylene or $C_2$-$C_3$ olefins using one-step direct conversion of the syngas, wherein the selectivity of $C_2$-$C_3$ olefins is 78-87%, and the selectivity of the ethylene is 75-82%, while the selectivity for a methane side product is very low (<9%), and the hydrocarbon selectivity of C4 and above is less than 10%.

The present invention has the following advantages:

(1) Different from the traditional technology for preparing the light olefin through methanol (MTO for short), the present invention realizes preparation of the ethylene through one-step direct conversion of the syngas.

(2) In the product of the present invention, a single ethylene product has high selectivity and can reach 75-82%, and high space time yield (the olefin yield is as high as 1.33 mmol/hg); and the product is easy to separate, and has a good application prospect.

(3) The metal oxide in the catalyst has a higher specific surface area; therefore, the metal oxide surface has more active sites, which is more conducive to conducting a catalytic reaction.

(4) On one hand, the role of the component II in the catalyst is to further convert the active gas-phase intermediate produced by the component I to obtain light olefin by coupling with the component I. The role of the component II on the balanced pull of the series reaction can promote the activation and conversion of the component I for the syngas and thus can increase the conversion rate. On the other hand, the special porous channel structure of the zeolite in the component II used in the present invention has a unique selection effect and can obtain more ethylene products with high selectivity.

(5) The functions of the present invention cannot be achieved if the component I or the component II in the present invention is used separately. For example, the selectivity of methane in the product after separate use of the component I is very high, and the conversion rate is very low.

The syngas cannot be activated and converted if the component II is used separately. Only the synergistic catalysis of the component I and the component II can achieve efficient conversion of the syngas and obtain excellent selectivity. Because the component I can activate the syngas to generate a specific active gas-phase intermediate, the intermediate diffuses into the porous channel of the component II through the gas phase. The zeolite of the MOR topology selected in the present invention has special pore structure and acidity which can effectively further activate and convert the active gas-phase intermediate produced by the component I into olefin. The special porous channel structure of the component II enables the product to have special selectivity.

(6) The component II in the catalyst of the present invention is modified with the fatty amine; the selectivity of the single component of ethylene obtained by catalytic conversion of the syngas is as high as 75-82%, and the selectivity of methane is less than 9%; and the selectivity of hydrocarbons above $C_4$ is greatly suppressed to be less than 10%.

DETAILED DESCRIPTION OF PREFERRED EMBODIMENTS

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

Embodiment 1

I. Preparation of Component I

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

The specific surface area of the sample can be tested through a physical adsorption method of nitrogen or argon.

The metal oxide in the present invention can be obtained by purchasing a commercially available metal oxide with a high specific surface area, or obtained by the following methods:

I. Preparation of Component I of Catalyst (I) ZnO material with high specific surface area was synthesized through a precipitation method:

(1) 3 parts of 0.446 g (1.5 mmol) of $Zn(NO_3)_2 \cdot 6H_2O$ were respectively weighed into three containers; 0.300 g (7.5 mmol), 0.480 g (12 mmol) and 0.720 g (18 mmol) of NaOH were respectively weighed and successively added to the above three containers; 30 ml of deionized water was weighed and added to the three containers; stirring was conducted for a time greater than 0.5 h at 70° C. to uniformly mix a solution; natural cooling was conducted to room temperature; reaction liquid was centrifugally separated to collect the centrifugally separated precipitate; and washing was conducted with deionized water twice to obtain ZnO metal oxide precursor;

(2) roasting: after drying the obtained product in the air, the product was roasted in an atmosphere to obtain ZnO material with high specific surface area. The atmosphere is inert gas, reducing gas or oxidizing gas. The inert gas is one or more than one of $N_2$, He and Ar. The reducing gas is one or two of $H_2$ and CO, and the reducing gas may also contain the inert gas. The oxidizing gas is one or more than one of $O_2$, $O_3$ and $NO_2$, and the oxidizing gas may also contain the inert gas. Roasting temperature is 300-700° C., and time is 0.5 $h^{-12}$ h.

The purpose of roasting is to decompose the precipitated metal oxide precursor into oxide nanoparticles with high specific surface area at high temperature, and clean the adsorbed species on the surface of the oxide generated by decomposition through the high temperature roasting treatment.

Specific samples and preparation conditions thereof are shown in Table 1 below. As a reference example, ZnO #4 in the table is a commercially available ZnO single crystal with low specific surface area.

TABLE 1

Preparation of ZnO Material and Parameter Performance

| Zinc Oxide Sample Number | Roasting Time/h | Roasting Temperature/° C. | Roasting Atmosphere | Specific Surface Area $m^2/g$ |
|---|---|---|---|---|
| ZnO#1 | 5 | 500 | Ar | 71 |
| ZnO#2 | 2 | 320 | 5% $H_2/N_2$ | 47 |
| ZnO#3 | 3 | 550 | Air | 15 |
| ZnO#4 | — | — | | <1 |

(II) MnO material with high specific surface area was synthesized through a coprecipitation method:

The preparation process is the same as that of the above ZnO #2. The difference is that, the precursor of Zn is changed for the corresponding precursor of Mn, which may be one of manganous nitrate, manganese chloride and manganese acetate, and is manganous nitrate herein. The corresponding product is defined as MnO. The specific surface area is 23 $m^2/g$.

(III) $CeO_2$ material with high specific surface area was synthesized through a coprecipitation method:

The preparation process is the same as that of the above ZnO #2. The difference is that, the precursor of Zn is changed for the corresponding precursor of Ce, which may be one of cerium nitrate, cerium chloride and cerous acetate, and is cerium nitrate herein. The corresponding product is defined as $CeO_2$. The specific surface area is 92 $m^2/g$.

(IV) $Ga_2O_3$ material with high specific surface area was synthesized through a coprecipitation method:

The preparation process is the same as that of the above ZnO #2. The difference is that, the precursor of Zn is changed for the corresponding precursor of Ga, which may be one of gallium nitrate, gallium chloride and gallium acetate, and is gallium nitrate herein. The corresponding product is defined as $Ga_2O_3$. The specific surface area is 55 $m^2/g$.

(V) $Bi_2O_3$ material with high specific surface area was synthesized through a coprecipitation method:

The preparation process is the same as that of the above ZnO #2. The difference is that, the precursor of Zn is changed for the corresponding precursor of Bi, which may be one of bismuth nitrate, bismuth chloride and bismuth acetate, and is bismuth nitrate herein. The corresponding product is defined as $Bi_2O_3$. The specific surface area is 87 $m^2/g$.

(VI) $In_2O_3$ material with high specific surface area was synthesized through a coprecipitation method:

The preparation process is the same as that of the above ZnO #2. The difference is that, the precursor of Zn is changed for the corresponding precursor of In, which may be one of indium nitrate, indium chloride and indium acetate, and is indium nitrate herein. The corresponding product is defined as $In_2O_3$. The specific surface area is 52 $m^2/g$.

(VII) $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn(1-a-b)O_x$ with high specific surface area were synthesized through a precipitation method Zinc nitrate, aluminum nitrate, chromic nitrate, manganese nitrate, zirconium nitrate, indium nitrate, cobalt nitrate and ferric nitrate were adopted as precursors, and mixed at room temperature in water (wherein for ammonium carbonate as a precipitant, a feeding ratio is excessive or the ratio of ammonium ions to metal ions is preferably 1:1). The above mixed solution was aged, and then taken out for washing, filtering and drying; and the obtained solid was roasted under an air atmosphere to obtain a metal oxide with high specific surface area. Specific samples and preparation conditions thereof are shown in Table 2 below.

TABLE 2

Preparation of Metal Oxide with High Specific Surface Area and Performance Parameters

| Metal Oxide | Feeding Ratio of Metal Elements and Final Molar Concentration of One Metal in Water (mmol/L) | Aging Temperature °C. | Aging Time h | Roasting Temperature °C. | Roasting Time h | Specific Surface Area m²/g |
|---|---|---|---|---|---|---|
| $ZnCr_2O_4$ | ZnCr = 1:2, Zn is 50 mM | 120 | 24 | 500 | 2 | 126 |
| $ZnAl_2O_4$ | ZnAl = 1:2, Zn is 50 mM | 130 | 20 | 400 | 4 | 137 |
| $ZnGa_2O_4$ | ZnGa = 1:2, Zn is 50 mM | 130 | 20 | 400 | 4 | 110 |
| $ZnIn_2O_4$ | ZnIn = 1:2, Zn is 50 mM | 130 | 20 | 400 | 4 | 87 |
| $MnCr_2O_4$ | MnCr = 1:2, Mn is 50 mM | 140 | 18 | 450 | 3 | 11 |
| $MnAl_2O_4$ | MnAl = 1:2, y = 2; and Mn is 50 mM | 145 | 16 | 400 | 2 | 15 |
| $MnZr2O_4$ | MnZr = 1:2, Mn is 50 mM | 150 | 12 | 500 | 1 | 38 |
| $MnIn_2O_4$ | MnIn = 1:2, Mn is 50 mM | 150 | 12 | 500 | 1 | 67 |
| $CoAl_2O_4$ | CoAl = 1:2, Co is 50 mM | 145 | 16 | 400 | 2 | 22 |
| $FeAl_2O_4$ | FeAl = 1:2, Fe is 50 mM | 145 | 16 | 400 | 2 | 30 |
| $InAl3MnO_7$ | In:Al:Mn = 1:3:1; Mn is 50 mM | 150 | 12 | 500 | 1 | 84 |
| $InGa_2MnO_7$ | In:Ga:Mn = 1:2:1; Mn is 50 mM | 145 | 16 | 400 | 2 | 67 |

(VIII) Metal oxide dispersed in dispersing agent $Cr_2O_3$, $Al_2O_3$ or $ZrO_2$ $Cr_2O_3$, $Al_2O_3$ or $ZrO_2$ dispersed metal oxide was prepared through a precipitate deposition method by taking $Cr_2O_3$, $Al_2O_3$ or $ZrO_2$ as a carrier. By taking preparation of dispersed ZnO as an example, commercial $Cr_2O_3$ (the specific surface area is about 5 m²/g), $Al_2O_3$ (the specific surface area is about 20 m²/g) or $ZrO_2$ (the specific surface area is about 10 m²/g) as a carrier was dispersed in water in advance, and then mixed and precipitated at room temperature with a sodium hydroxide precipitant by taking zinc nitrate as raw material. The molar concentration of $Zn^{2+}$ was 0.067M; and the ratio of molar fractions of $Zn^{2+}$ and the precipitant was 1:8; and then aging was conducted at 160° C. for 24 hours to obtain dispersed ZnO by taking $Cr_2O_3$, $Al_2O_3$ or $ZrO_2$ as the carrier (the contents of the dispersing agents in the component I are 0.1 wt %, 20 wt % and 85 wt %). The obtained sample was roasted at 500° C. for 1 hour in air. The products are successively defined as dispersed oxides 1-3, and the specific surface areas are successively 148 m²/g, 115 m²/g and 127 m²/g.

The same method is used to obtain dispersed MnO oxide by taking $SiO_2$ (the specific surface area is about 2 m²/g), $Ga_2O_3$ (the specific surface area is about 10 m²/g), or $TiO_2$ (the specific surface area is about 15 m²/g) as the carrier (the contents of the dispersing agents in the component I are 5 wt %, 30 wt % and 60 wt %). The products are successively defined as dispersed oxides 4-6. The specific surface areas are successively 97 m²/g, 64 m²/g and 56 m²/g.

The same method is used to obtain dispersed ZnO oxide by taking activated carbon (the specific surface area is about 1000 m²/g), graphene (the specific surface area is about 500 m²/g), or carbon nanotube (the specific surface area is about 300 m²/g) as the carrier (the contents of the dispersing agents in the component I are 5 wt %, 30 wt % and 60 wt %). The products are successively defined as dispersed oxides 7-9. The specific surface areas are successively 177 m²/g, 245 m²/g and 307 m²/g.

II. Preparation of Component II (Zeolite of MOR Topology)

The MOR topology is an orthorhombic crystal system, is of a one-dimensional porous channel structure with parallel elliptical straight-through porous channels, and includes 8-ring and 12-ring one-dimensional straight-through porous channels. 8-ring porous channel are communicated on the side edges of the 12-ring porous channels.

The MOR zeolite in the present invention may be a commercial zeolite which is purchased directly or a synthesized zeolite. Herein, MOR zeolite produced by Nankai University Catalyst Plant is used as MOR1; meanwhile, seven zeolites with MOR topology are also prepared by taking hydrothermal synthesis as an example.

The specific preparation process is:
aluminum sulphate was mixed with a sodium hydroxide solution according to $n(SiO_2)/n(Al_2O_3)=15$, $n(Na_2O)/n$ $(SiO_2)=0.2$, $n(H_2O)/n(SiO_2)=26$; then, silica sol was added and stirred for 1 h to obtain homogeneous phase initial gel; then, the solution was transferred into a high pressure synthesis kettle, statically crystallized at 180° C. for 24 h, quenched, washed and dried to obtain a mordenite sample labeled as Na-MOR.

Na-MOR was taken, mixed with 1 mol/L ammonium chloride solution, stirred at 90° C. for 3 h, washed, dried for four times in succession, and roasted at 450° C. for 6 h to obtain H-mordenite.

The skeleton element composition of the zeolite of the MOR topology prepared by the above process may be one of Si—Al—O, Ga—Si—O, Ga—Si—Al—O, Ti—Si—O, Ti—Al—Si—O, Ca—Al—O and Ca—Si—Al—O.

O element of part of the skeleton is connected with H, and corresponding products are successively defined as MOR1-8.

separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is selected from any of the following gas:

a) nitrogen and/or inert gas;
b) mixed gas of hydrogen, nitrogen and/or inert gas, with the volume of hydrogen in the mixed gas being 5-50%;
c) mixed gas of CO, nitrogen and/or inert gas, with the volume of CO in the mixed gas being 5-20%;

TABLE 3

Preparation of Zeolite of MOR Topology and Performance Parameters

| Sample Number | Si and Ca Sources | Al, Ga and Ti Sources | Molar Ratio | Hydrothermal Temperature (° C.) | Time (Day) |
|---|---|---|---|---|---|
| MOR2 | silica sol Ca(OH) | Al(OH)$_3$ | n(SiO$_2$ + CaO)/n(Al$_2$O$_3$) = 11, n(SiO$_2$)/n(CaO) = 43, n(Na2O)/n(SiO$_2$) = 0.2 n(H$_2$O)/n(SiO$_2$) = 26 | 180 | 1 |
| MOR3 | TEOS | AlOOH gallium nitrate | n(SiO$_2$)/n(AhO$_3$ + Ga$_2$O$_3$) = 12, n(Ga$_2$O$_3$)/n(AhO$_3$) = 7, n(Na2O)/n(SiO$_2$) = 0.3 n(H$_2$O)/n(SiO$_2$) = 26 | 170 | 1.3 |
| MOR4 | silica sol | titanium sol | n(SiO$_2$)/n(TiO$_2$) = 40, n(Na2O)/n(SiO$_2$) = 0.3 n(H2O)/n(SiO$_2$) = 26 | 185 | 1 |
| MOR5 | silica sol | aluminum sulfate | n(SiO$_2$)/n(Al$_2$O$_3$) = 8, n(Na2O)/n(SiO$_2$) = 0.2 n(H$_2$O)/n(SiO$_2$) = 27 | 185 | 1 |
| MOR6 | silica sol | aluminum nitrate | n(SiO$_2$)/n(Al$_2$O3) = 12, n(Na$_2$O)/n(SiO$_2$) = 0.2 n(H$_2$O)/n(SiO$_2$) = 23 | 180 | 1.1 |
| MOR7 | TEOS | aluminum sulfate | n(SiO$_2$)/n(Al$_2$O$_3$) = 17, n(Na$_2$O)/n(SiO$_2$) = 0.2 n(H$_2$O)/n(SiO$_2$) = 28 | 175 | 1.5 |
| MOR8 | silica sol | titanium sol AlOOH | n(SiO$_2$)/n(Al2O$_3$ + TiO$_2$) = 15, n(TiO$_2$)/n(AhO$_3$) = 1, n(Na$_2$O)/n(SiO$_2$) = 02n(H$_2$O)/n(SiO$_2$) = 25 | 175 | 0.7 |

A proper quantity of the prepared zeolite was dehydrated and degassed under vacuum at temperature of 400° C. and pressure of 10–4 Pa. After 10 h, when the temperature was reduced to 300° C., 200 Pa of organic base gas was introduced into a vacuum chamber. After balance for 10 h, desorption was conducted at the same temperature for 1 h.

MOR1, MOR2, MOR3, MOR4, MOR5, MOR6, MOR7 and MOR8 were treated with dimethylamine, trimethylamine, diethylamine, triethylamine, ethylenediamine, monopropylamine, dipropylamine, tripropylamine, isopropylamine, diisopropylamine, 1,2-dimethylpropylamine, 1,2-propanediamine, 2-propeneamine, cyclopropylamine, n-butylamine, di-n-butylamine, isobutylamine, sec-butylamine, 1,4-butanediamine, tert-butylamine, diisobutylamine hexylamine, 2-ethylhexylamine, hexamethylenediamine and trioctylamine to respectively obtain MOR9, MOR10, MOR11, MOR12, MOR13, MOR14, MOR15, MOR16, MOR17, MOR18, MOR19, MOR20, MOR21, MOR22, MOR23, MOR24, MOR25, MOR26, MOR27, MOR28, MOR29, MOR30, MOR31 and MOR32.

III. Catalyst Preparation

The component I and the component II in the required ratio were added to the container to achieve the purposes of d) mixed gas of O$_2$, nitrogen and/or inert gas, with the volume of O$_2$ in the mixed gas being 5-20%, wherein the inert gas is one or more than one of helium, argon and neon.

The mechanical mixing can adopt one or more than one of mechanical agitation, ball milling, rocking bed mixing and mechanical grinding for composition. Specifically:

Mechanical stirring: mixing the component I and the component II with a stirring rod in a stirring tank; and regulating the mixing degree of the component I and the component II by controlling stirring time (5 min-120 min) and rate (30-300 r/min).

Ball milling: rolling at high speed in a grinding tank by using abrasive and the catalysts; and producing strong impact and milling on the catalysts to achieve the effects of dispersing and mixing the component I and the component II. The ratio of the abrasive (which is stainless steel, agate and quartz; and the size range is 5 mm-15 mm) to the catalysts (the mass ratio range is 20-100:1) is controlled.

Shaking table mixing: premixing the component I and the component II and placing the components into the container; realizing the mixing of the component I and the component II by controlling the reciprocating oscillation or circumferential oscillation of a shaking table; and realizing uniform mixing by regulating oscillation speed (range: 1-70 r/min) and time (range: 5 min-120 min).

Mechanical grinding: premixing the component I and the component II and placing the components into the container; and under certain pressure (range: 5 kg-20 kg), making relative motion (speed range: 30-300 r/min) by an abrader and mixed catalysts to achieve the effect of uniform mixing. Specific catalyst preparation and parameter features are shown in Table 4.

TABLE 4

Preparation of Catalysts and Parameter Features

| Catalyst Number | Component I | Component II | Weight Ratio of I to II | Compounding Mode and Condition | | | |
|---|---|---|---|---|---|---|---|
| | | | | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| A | ZnO#1 | MOR9 | 0.33 | 5, 30 | | | |
| B | ZnO#2 | MOR10 | 0.5 | 100, 250 | | | |
| C | ZnO#3 | MOR11 | 2 | | 5 mm stainless steel ball, 50:1 | | |
| D | MnO | MOR12 | 1 | | 6 mm stainless steel ball, 60:1 | | |
| E | $CeO_2$ | MOR13 | 1 | | | 5, 10 | |
| F | $Bi_2O_3$ | MOR14 | 3 | | | 60, 100 | |
| G | $In_2O_3$ | MOR15 | 3 | | | | 5, 30 |
| H | $Ga_2O_3$ | MOR16 | 1 | 100, 300 | | | |
| I | $ZnCr_2O_4$ | MOR17 | 5 | | 6 mm agate ball, 100:1 | | |
| J | $ZnAl_2O_4$ | MOR18 | 1 | | | 70, 100 | |
| K | $ZnGa_2O_4$ | MOR19 | 3 | | | | 15, 200 |
| L | $ZnIn_2O_4$ | MOR20 | 0.33 | | | | 20, 300 |
| M | $MnCr_2O_4$ | MOR21 | 1 | 100, 300 | | | |
| N | $MnAl_2O_4$ | MOR22 | 3 | | 6 mm quartz, 100:1 | | |
| O | $MnZr_2O_4$ | MOR23 | 0.33 | | 6 mm quartz, 100:1 | | |
| P | $MnIn_2O_4$ | MOR24 | 1 | | | | 10, 100 |
| Q | $CoAl_2O_4$ | MOR25 | 1 | | | 5, 10 | |
| R | $FeAl_2O_4$ | MOR26 | 3 | | | 60, 100 | |
| S | $InAl_3MnO_7$ | MOR27 | 3 | | | | 5, 30 |
| T | $InGa_2MnO_7$ | MOR28 | 1 | 100, 300 | | | |
| U | dispersed oxide 1 | MOR29 | 0.33 | | 6 mm quartz, 100:1 | | |
| V | dispersed oxide 2 | MOR30 | 1 | 100, 250 | | | |
| W | dispersed oxide 3 | MOR31 | 3 | | 5 mm stainless steel ball, 50:1 | | |
| X | dispersed oxide 4 | MOR32 | 1 | | | | 10, 100 |
| Y | dispersed oxide 5 | MOR9 | 4 | | | 50, 60 | |
| Z | dispersed oxide 6 | MOR9 | 3 | | | | 10, 100 |
| Z1 | dispersed oxide 7 | MOR9 | 20 | | 5 mm stainless steel ball, 100:1 | | |
| Z2 | dispersed oxide 8 | MOR9 | 16 | 100, 200 | | | |
| Z3 | dispersed oxide 9 | MOR9 | 0.1 | | | | 20, 100 |
| Reference example 1 | ZnO#4 | MOR24 | 3 | | | 20, 30 | |
| Reference example 2 | $MnCr_2O_4$ | MOR1 | 1 | | | 5, 10 | |
| Reference example 3 | $MnAl_2O_4$ | MOR2 | 1 | | | 5, 10 | |
| Reference example 4 | $MnZr_2O_4$ | MOR3 | 1 | | | 5, 10 | |
| Reference example 5 | $MnIn_2O_4$ | MOR4 | 1 | | | 5, 10 | |

TABLE 4-continued

Preparation of Catalysts and Parameter Features

| Catalyst Number | Component I | Component II | Weight Ratio of I to II | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
|---|---|---|---|---|---|---|---|
| Reference example 6 | CoAhO$_4$ | MOR5 | 1 | | | 5, 10 | |
| Reference example 7 | FeAl$_2$O$_4$ | MOR6 | 1 | | | 5, 10 | |
| Reference example 8 | InA13MnO$_7$ | MOR7 | 1 | | | 5, 10 | |
| Reference example 9 | InGa$_2$MnO$_7$ | MOR8 | 1 | | | 5, 10 | |
| Reference example 10 | composite metal ZnCo, the molar ratio of Zn to Co is 1:1. | MOR11 | 2 | | 5 mm stainless steel ball, 50:1 | | |
| Reference example 11 | TiO$_2$ | MOR11 | 2 | | 5 mm stainless steel ball, 50:1 | | |

Example of Catalytic Reactions

A fixed bed reaction is taken as an example, but the catalyst is also applicable to a fluidized bed reactor. The apparatus was equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the H$_2$ atmosphere, and then the syngas (H2/CO molar ratio=0.2-3.5) was switched. The syngas can also include CO$_2$, wherein the volume concentration of CO$_2$ in the syngas is 0.1-50%. The pressure of the syngas is 0.5-10 MPa. The temperature is raised to reaction temperature of 300-600° C., and the space velocity of the reaction raw gas is regulated to 300-10000 ml/g/h. On-line chromatography is used to detect and analyze the product.

The reaction performance can be changed by changing the temperature, pressure and space velocity. The selectivity of the ethylene and the propylene in the product is as high as 78-87%, and the conversion rate of the raw material is 10-60%. Due to the effective synergy between the zeolite and the oxide, mass production of the methane and C$_{4+}$ hydrocarbons is avoided.

TABLE 5

Application and Effect of Catalysts

| Embodiment | Catalyst | GHSV (h$^{-1}$) | Temperature (° C.) | H2/CO MOLAR RATIO | Pressure (MPa) | Ethylene Space Time Yield (mmol Olefin/h · g Catalyst) | Ethylene and Propylene Selectivities % | CH4 Selectivity % | Ethylene Selectivity % | C$_{4+}$ Selectivity % |
|---|---|---|---|---|---|---|---|---|---|---|
| 1 | A | 3500 | 420 | 2.5 | 8 | 0.67 | 83 | 7 | 75 | 5 |
| 2 | B | 3000 | 480 | 1.5 | 3 | 0.63 | 81 | 5 | 76 | 6 |
| 3 | C | 4500 | 410 | 1 | 4 | 0.37 | 78 | 2 | 79 | 4 |
| 4 | D | 5000 | 370 | 3.5 | 9 | 0.32 | 79 | 3 | 76 | 8 |
| 5 | E | 3000 | 470 | 0.5 | 5 | 0.75 | 82 | 4 | 75 | 7 |
| 6 | F | 3500 | 410 | 2 | 4 | 0.68 | 82 | 4 | 76 | 8 |
| 7 | G | 3000 | 450 | 1 | 6 | 0.33 | 78 | 8 | 75 | 9 |
| 8 | H | 2500 | 360 | 1 | 5 | 0.38 | 78 | 9 | 75 | 9 |
| 9 | I | 7500 | 410 | 2.5 | 5 | 0.99 | 87 | 6 | 81 | 4 |
| 10 | J | 4000 | 350 | 3 | 7 | 1.11 | 86 | 4 | 81 | 3 |
| 11 | K | 3000 | 370 | 2.5 | 3 | 1.28 | 86 | 2 | 81 | 3 |
| 12 | L | 2500 | 350 | 3 | 3.5 | 0.79 | 83 | 5 | 76 | 6 |
| 13 | M | 3500 | 410 | 3.5 | 0.9 | 0.31 | 78 | 9 | 75 | 6 |
| 14 | N | 4000 | 400 | 2 | 2.5 | 0.34 | 78 | 9 | 76 | 6 |
| 15 | O | 2500 | 520 | 1 | 8 | 0.54 | 80 | 8 | 75 | 5 |
| 16 | P | 2500 | 400 | 3.5 | 1.5 | 0.73 | 83 | 7 | 76 | 3 |
| 17 | Q | 3000 | 400 | 0.5 | 7 | 0.51 | 79 | 7 | 76 | 5 |
| 18 | R | 3500 | 360 | 2.5 | 7.5 | 0.41 | 79 | 8 | 76 | 9 |
| 19 | S | 8500 | 350 | 2.5 | 5 | 0.67 | 85 | 5 | 82 | 5 |
| 20 | T | 1000 | 450 | 1 | 3.5 | 0.58 | 84 | 8 | 81 | 6 |
| 21 | U | 2500 | 410 | 1.5 | 7 | 0.93 | 87 | 3 | 75 | 5 |

TABLE 5-continued

Application and Effect of Catalysts

| Embodiment | Catalyst | GHSV ($h^{-1}$) | Temperature (° C.) | H2/CO MOLAR RATIO | Pressure (MPa) | Ethylene Space Time Yield (mmol Olefin/h · g Catalyst) | Ethylene and Propylene Selectivities % | CH4 Selectivity % | Ethylene Selectivity % | $C_{4+}$ Selectivity % |
|---|---|---|---|---|---|---|---|---|---|---|
| 22 | V | 3000 | 380 | 1 | 6 | 0.99 | 86 | 6 | 78 | 3 |
| 23 | W | 500 | 370 | 4 | 5 | 1.10 | 85 | 4 | 75 | 6 |
| 24 | X | 2500 | 350 | 2.5 | 5 | 1.08 | 86 | 6 | 75 | 4 |
| 25 | Y | 2000 | 410 | 1 | 7 | 1.05 | 86 | 2 | 81 | 4 |
| 26 | Z | 1500 | 430 | 2.5 | 3 | 0.99 | 86 | 3 | 77 | 4 |
| 27 | Z1 | 4000 | 400 | 2 | 3.5 | 0.13 | 78 | 8 | 75 | 7 |
| 28 | Z2 | 3000 | 430 | 3.5 | 0.9 | 0.11 | 79 | 7 | 75 | 8 |
| 29 | Z3 | 10000 | 370 | 2 | 2.5 | 0.12 | 78 | 9 | 75 | 7 |
| 30 | J | 2500 | 370 | 1.5 ($CO_2$ concentration of 1%) | 5 | 0.99 | 85 | 7 | 80 | 5 |
| 31 | K | 4000 | 370 | 1 ($CO_2$ concentration of 45%) | 7 | 0.90 | 87 | 5 | 83 | 4 |
| 32 | Reference example 1 | 1000 | 300 | 0.5 | 1 | 0.02 | 35 | 55 | 20 | 3 |
| 33 | Reference example 2 | 1000 | 430 | 1 | 2 | 0.47 | 80 | 7 | 75 | 10 |
| 34 | Reference example 3 | 4000 | 450 | 3 | 3 | 0.28 | 80 | 6 | 75 | 11 |
| 35 | Reference example 4 | 2000 | 350 | 2.5 | 3 | 0.35 | 81 | 6 | 76 | 9 |
| 36 | Reference example 5 | 2000 | 400 | 0.5 | 7 | 0.37 | 75 | 6 | 73 | 15 |
| 37 | Reference example 6 | 2000 | 360 | 2.5 | 2.5 | 0.31 | 76 | 11 | 75 | 10 |
| 38 | Reference example 7 | 2000 | 400 | 1 | 4 | 0.59 | 80 | 11 | 75 | 7 |
| 39 | Reference example 8 | 2000 | 370 | 0.5 | 9 | 0.54 | 80 | 10 | 75 | 6 |
| 40 | Reference example 9 | 3000 | 470 | 3 | 3 | 0.30 | 80 | 10 | 75 | 7 |
| 41 | Reference example 10 | 3000 | 450 | 2 | 4 | 0.53 | 18 | 32 | 10 | 40 |
| 42 | Reference example 11 | 2000 | 450 | 1 | 6 | 0.01 | 21 | 66 | 7 | 5 |
| 43 | Reference example 12 | 3000 | 450 | 2.5 | 4 | <0.01 | 1.2 | 50 | 0.8 | 1.1 |
| 44 | Reference example 13 | 2200 | 450 | 3 | 2 | <0.01 | — | — | — | — |

The reaction results of reference examples 2-9 show that MOR which is post-processed by the fatty amine has a significant effect on the regulation of catalytic performance. Compared with the catalysts which are not regulated with the fatty amine, the regulated catalyst significantly reduces the selectivity of the methane and hydrocarbons above $C_4$ and also improves the selectivity of the light olefin and the ethylene.

The component I in the catalyst adopted in reference example 10 is metal ZnCo. The molar ratio of ZnCo is 1:1. Other parameters and the mixing process are the same as those of catalyst C.

The component I in the catalyst adopted in reference example 11 is $TiO_2$. Other parameters and the mixing process are the same as those of catalyst C.

The catalyst adopted in reference example 12 is a sample containing only component I ZnO #1 without the MOR zeolite, and the reaction conversion rate is very low. The products mainly comprise by-products such as dimethyl ether and methane, and almost no ethylene is produced.

The catalyst adopted in reference example 13 is a metal oxide containing only MOR9 zeolite of component II without the component I and acting as an active ingredient, and the catalytic reaction almost has no activity.

Reference examples 12 and 13 indicate that reaction effects are extremely poor when only component I or component II exists, and do not have the excellent reaction performance in the present invention.

The above embodiments are provided only for the purpose of describing the present invention, and are not intended to limit the scope of the present invention. The scope of the present invention is defined by the appended claims. Various equivalent replacements and amendments made without departing from the spirit and the principle of the present invention shall be covered within the scope of the present invention.

The invention claimed is:

1. A catalyst, comprising a component I and a component II, which are compounded in a mechanical mixing mode; wherein, an active ingredient of the component I is a metal oxide; the component II is a zeolite of MOR topology; in the component II, the zeolite of the MOR topology is modified with an amine selected from the group consisting of dimethylamine, trimethylamine, diethylamine, triethylamine, ethylenediamine, monopropylamine, dipropylamine, tripropylamine, isopropylamine, diisopropylamine, 1,2-dimethylpropylamine, 1,2-propanediamine, 2-propeneamine, cyclopropylamine, n-butylamine, di-n-butylamine, isobutylamine, sec-butylamine, 1,4-butanediamine, tert-butylamine, diisobutylaminehexylamine, 2-ethylhexylamine, hexamethylenediamine, trioctylamine, and combinations thereof;

the modification with the amine is to disperse the amine into B acid sites in 12-ring porous channels of the zeolite of the MOR topology.

2. The catalyst according to claim 1, wherein
the metal oxide is at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$, and $In_aGa_bMn_{(1-a-b)}O_x$;
a specific surface area of $MnO_x$, $ZnO_x$, $CeO_x$, $GaO_x$, $BiO_x$ and $InO_x$ is 1-100 m$^2$/g;
a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 5-150 m$^2$/g;
a value range of x is 0.7-3.7, and a value range of a is 0-1; and a value range of a+b is 0-1.

3. The catalyst according to claim 1, wherein a weight ratio of the active ingredient in the component I to the component II is 0.1-20.

4. The catalyst according to claim 1, wherein a dispersing agent is also added to the component I; the dispersing agent is at least one of $Al_2O_3$, $SiO_2$, $Cr_2O_3$, $ZrO_2$, $TiO_2$, $Ga_2O_3$, activated carbon, graphene, and carbon nanotube; the metal oxide is dispersed in the dispersing agent; and the content of the dispersing agent in the component I is 0.05-90 wt %;
and the balance is an active metal oxide.

5. The catalyst according to claim 1, wherein the skeleton element composition of the zeolite of the MOR topology is at least one of Si—Al—O, Ga—Si—O, Ga—Si—Al—O, Ti—Si—O, Ti—Al—Si—O, Ca—Al—O, and Ca—Si—Al—O.

6. A method for producing a light olefin product comprising converting syngas to the light olefin product in the presence of the catalyst of claim 1, wherein the light olefin product comprises ethylene.

7. The method according to claim 6, wherein the converting is conducted under a pressure of 0.5-10 MPa, reaction temperature of 300-600° C., a space velocity of 300-10000 h$^{-1}$, the syngas is a H2/CO mixture with a molar ratio of H2/CO of 0.2-3.5.

8. The method according to claim 6, wherein the light olefin product comprises $C_{2-4}$ olefin, and the method achieves a selectivity of the ethylene of 75-82%, a selectivity of a methane side product of less than 9%, and a selectivity of hydrocarbon products with more than 4 C atoms of less than 10%.

9. The catalyst according to claim 2, wherein the specific surface area of $MnO_x$, $ZnO_x$, $CeO_x$, $GaO_x$, $BiO_x$ and $InO_x$ is 50-100 m$^2$/g, and the specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 50-150 m$^2$/g.

10. The catalyst according to claim 3, wherein the weight ratio of the active ingredients ingredient in the component I to the component II is 0.3-8.

11. The method according to claim 7, wherein the pressure is 1-8 MPa, the reaction temperature is 300° C. -450° C., the space velocity is 500-9000 h$^{-1}$, the molar ratio of H2/CO is 0.3-2.5, and the syngas also comprises $CO_2$, and a volume concentration of $CO_2$ in the syngas is 0.1-50%.

12. The method according to claim 7, wherein the pressure is 2-8 MPa, and the space velocity is 500-6000 h$^{-1}$.

* * * * *